(12) United States Patent
Lenz

(10) Patent No.: US 6,417,679 B1
(45) Date of Patent: Jul. 9, 2002

(54) CONDUCTIVITY SENSOR

(75) Inventor: Jörg Lenz, Rauschenberg (DE)

(73) Assignee: PharmaSerV Marburg GmbH & Co. KG, Marburg (DE)

( * ) Notice: Subject to any disclaimer, the term of this patent is extended or adjusted under 35 U.S.C. 154(b) by 0 days.

(21) Appl. No.: 09/669,884

(22) Filed: Sep. 27, 2000

(30) Foreign Application Priority Data

Sep. 28, 1999 (DE) .......................... 199 46 315

(51) Int. Cl.$^7$ .............................................. G01N 27/42
(52) U.S. Cl. .................... 324/722; 324/715; 324/444
(58) Field of Search ................ 324/722, 691, 324/693, 71.1, 695, 715, 444, 446, 449

(56) References Cited

U.S. PATENT DOCUMENTS

| | | | | |
|---|---|---|---|---|
| 2,084,772 A | * | 6/1937 | Marden .................... | 313/11 |
| 3,467,590 A | * | 9/1969 | Gibson | |
| 3,601,693 A | | 8/1971 | Lorentzen | |
| 4,015,199 A | | 3/1977 | Rommel | |
| 4,118,663 A | | 10/1978 | Barben, II | |
| 4,212,045 A | * | 7/1980 | Martzloff ................... | 338/21 |
| 4,422,335 A | * | 12/1983 | Ohnesorge et al. ...... | 361/283.1 |
| 4,567,704 A | * | 2/1986 | Bernett et al. ............. | 428/49 |
| 4,691,169 A | * | 9/1987 | Baum ........................ | 324/448 |
| 5,025,219 A | | 6/1991 | Gaspard | |
| 5,085,217 A | * | 2/1992 | Shimizu ..................... | 600/391 |
| 5,685,482 A | * | 11/1997 | Sickles ...................... | 239/296 |
| 6,144,211 A | * | 11/2000 | Mohr ......................... | 324/642 |
| 6,281,689 B1 | * | 8/2001 | Chase et al. ............... | 324/691 |

FOREIGN PATENT DOCUMENTS

DE  25 21 009  12/1975

\* cited by examiner

Primary Examiner—N. Le
Assistant Examiner—Vincent Q. Nguyen
(74) Attorney, Agent, or Firm—Wenderoth, Lind & Ponack, L.L.P.

(57) ABSTRACT

The invention relates to a conductivity sensor with a substantially circular cylindrical casing of synthetic material and with metal measuring electrodes in its planar substantially circular front wall, of which at least two voltage electrodes and at least two current electrodes form poles, wherein at least two substantially circular voltage electrodes are encompassed by at least two plane-form current electrodes extending substantially in a semicircle or by at least four substantially circular current electrodes disposed in two semicircles.

12 Claims, 1 Drawing Sheet

CONDUCTIVITY SENSOR

BACKGROUND OF THE INVENTION

1. Field of the Invention

The invention relates to a conductivity sensor with a substantially circularly cylindrical casing of synthetic material and with metal measuring electrodes in its planar, substantially circular front wall, of which at least two voltage electrodes and at least two current electrodes form poles.

2. Description of the Related Art

Such known conductivity sensors entail the problem that they project into the reaction vessels and thus hinder the cleaning operation, which is especially critical in the case of pharmaceutical agents. In addition, they cannot be used, for example, in a thawing vessel filled with floating, ice chips, since they might be damaged. In fiber-containing media, the known sensors become clogged and can therefore not be used at all or only with special cleaning devices. This leads to a considerable technical expenditure and thus to an increase in costs. Furthermore, using the known conductivity sensors impairs the flow of the media current into which they project.

SUMMARY OF THE INVENTION

It is an object of the present invention to provide a conductivity sensor of the above described type which has low structural expenditure, avoids the cited disadvantages and yet has satisfactory sensitivity.

This task is solved in a conductivity sensor of the above described type by encompassing the at least two substantially circular voltage electrodes with at least two plane-form current electrodes extending substantially in a semicircle or by at least four current electrodes substantially circular and disposed in two semicircles.

Consequently, the invention provides an entirely novel measuring electrode configuration as a solution to the problems associated with the prior art. In spite of smaller cross sectional dimensions, a large measuring range of up to 850 milli Siemens (mS) can be covered such that application in the most diverse installations is possible. Due to the nearly planar surface of the front wall, the conductivity sensor according to the invention can be readily cleaned and is immune to contamination. It is, moreover, mechanically extraordinarily rugged. The interconnection can take place as four-pole or a two-pole conductivity sensor. In the configuration of individual circular current electrodes in two semicircles about the voltage electrodes, a closer approximation takes place to two plane-form current electrodes, substantially extending in a semicircle, the more poles are used. The number of measuring electrodes can also be varied in order to attain adaptation to special conditions. In the special configuration of the invention, the electrodes the measuring electrode area is markedly smaller than in conventional conductivity sensors and the voltage electrodes disposed on the inside are integrated better into the measuring field. The conductivity sensor according to the invention further has no beam shadow and can therefore also be used in fermenters which are equipped with CIP (Cleaning in Process).

In a special embodiment of the invention, two voltage electrodes are disposed at a distance from one another, and one of the two voltage electrodes has a nearly semicircularly encircling current electrode associated therewith.

The voltage electrodes and the semicircularly extending current electrodes mirror one another, wherein they are preferably symmetrically disposed on one and the same diameter of the front wall.

According to a further preferred embodiment of four or six substantially circular current electrodes, two or three of the substantially circular current electrodes are in a semicircular configuration about two voltage electrodes disposed at a distance from one another.

The substantially circular voltage electrodes are therein preferably disposed on a diameter of the front wall and the four or six current electrodes are preferably disposed on, or mirror-symmetrically with respect to, this diameter.

A further characteristic of the invention is that the temperature sensor is built into one of the measuring electrodes itself.

If the casing comprises an insulating synthetic material, such as polyether ether ketone (PEEK), glass or a comparably resistant insulator, and the measuring electrodes comprise special steel, tantalum, Hastelloy (a nickel-molybdenum-iron alloy known by this trademark), artificial carbon or like conductors resistant to liquids, the conductivity sensor conforms to FDA standards. In addition, its use up to 200° C. is possible and chemical resistivity is ensured, such that application in many fields under chemical and physical load is possible. Furthermore, all of the materials can be autoclaved up to at least 140° C.

Further, due to its small diameter, the casing can fit into a 25 mm connection socket such that the application on many fermenters can take place without requiring enclosures.

With a short installation length of less than approximately 10 mm, the danger of damage and interference with the media current is only minimal.

BRIEF DESCRIPTION OF THE DRAWINGS

Further objectives, characteristics, advantages and application feasibilities of the invention are evident based on the following description of embodiment examples in conjunction with the drawing. All described and/or graphically depicted characteristics by themselves or in any combination form the subject matter of the invention independently of their recapitulation in individual claims or their reference back.

In the drawings.

DETAILED DESCRIPTION OF THE INVENTION

Figure 1:
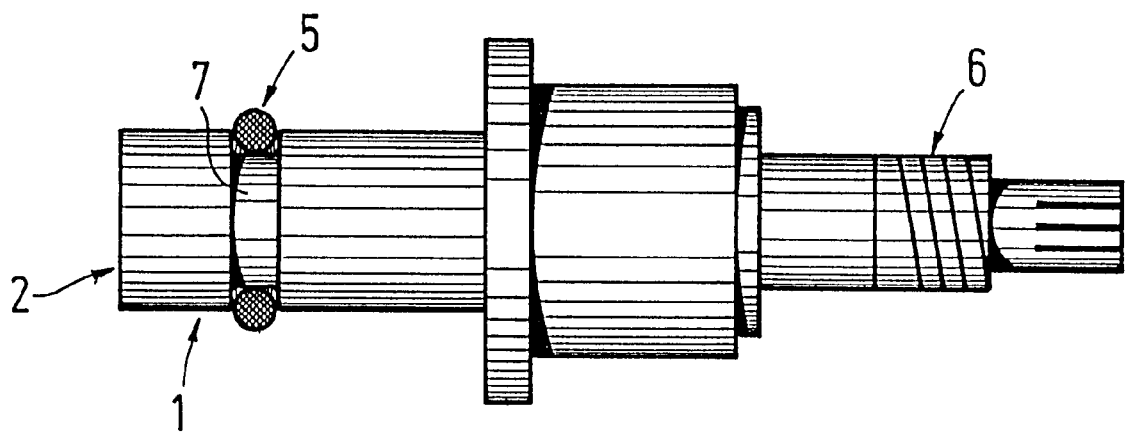
FIG. 1 is a side view schematic of a conductivity sensor in accordance with the present invention.

The conductivity sensor depicted in FIG. 1. comprises a casing 1 of a resistant insulator, which includes a circularly cylindrical circumferential wall and a planar front wall 2. In a circumferential groove 7 of the casing 1 is received a sealing ring 5 of silicon or the like material. Adjoining the casing 1 at the rear is a connector plug (VP connector) 6, which can-readily be cleaned and is immune to moisture.

Figure 2A:
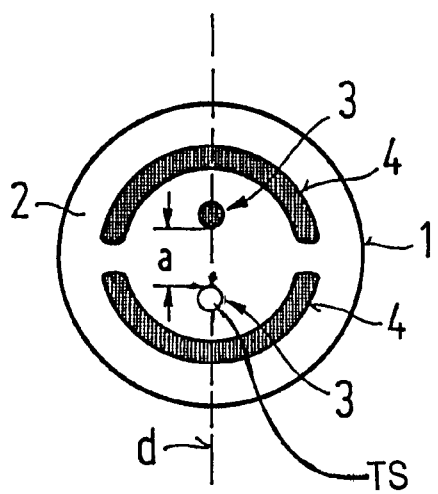
FIGS. 2a and 2b are two variants of the measuring electrode configuration provided according to the invention.
Figure 2B:
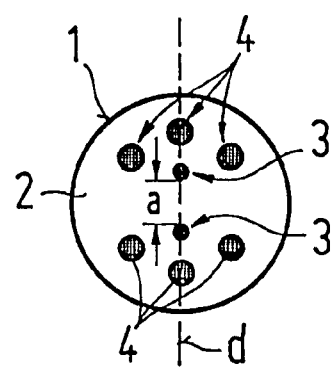

As is evident in FIGS. 2a and 2b, in the planar front wall 2 are disposed plane-form voltage electrodes 3 and current electrodes 4. The two circular voltage electrodes 3, disposed at the inside, have an inner clearance distance a from one another which, depending on the application, is between 1 and 10 mm. The two semicircular current electrodes 4 according to FIG. 2a, which are each assigned to one voltage electrode 3, have a minimum distance from the voltage electrodes 3 which is less than the inner clearance distance at the voltage electrodes 3 from one another. The distance of the semicircular current electrodes 4 of FIG. 2a from the outer edge of the front wall 2 is approximately equal to the minimum distance of the current electrodes 4 from the voltage electrodes 3.

The electrode configuration according to FIG. 2b is similar to that of FIG. 2a in so far as the semicircular current electrodes 4 according to FIG. 2a are replaced by individual circular current electrodes 4 according to FIG. 2b; however, the latter are also disposed semicircularly wherein in the depicted case three circular current electrodes 4 of a voltage electrode 3 are disposed partially encompassing them.

In the configuration according to FIG. 2a the voltage electrodes are disposed on a diameter d or axis of symmetry of the front wall 2 and the semicircular current electrodes 4 mirror-symmetrically on this same diameter d. In the configuration according to FIG. 2b the voltage electrodes 3 as well as two circular current electrodes 4 are disposed on one and the same diameter d of the front wall 2, while the, in each instance, two other circular current electrodes 4 are disposed mirror-symmetrically with respect to the diameter.

A temperature sensor T is built into one of the measuring electrodes 3, 4.

LIST OF REFERENCE SYMBOLS

1 Casing
2 Front wall
3 Voltage electrodes
4 Current electrodes
5 Sealing ring
6 Connector Plug
7 Circumferential groove
a Distance
d Diameter

What is claimed is:

1. A conductivity sensor comprising:
   a substantially cylindrical casing of synthetic material; and
   metal measuring electrodes in a planar and substantially circular front wall of said casing;
   wherein said measuring electrodes comprise at least two substantially circular voltage electrodes and at least two current electrodes forming poles;
   wherein said at least two voltage electrodes are encompassed by one of (a) said at least two current electrodes extending in a plane form and substantially in a semicircle, and (b) said at least two current electrodes including at least four substantially circular current electrodes that are disposed in two semicircles.

2. The sensor of claim 1, and further comprising a temperature sensor built into one of said measuring electrodes.

3. The sensor of claim 1, wherein one of said at least two voltage electrodes, which are disposed at a clearance distance from each other, corresponds to one of said at least two current electrodes extending in a plane form and substantially in a semicircle.

4. The sensor of claim 3, wherein said at least two voltage electrodes are disposed on a diameter of said front wall and said at least two current electrodes extending in a plane form and substantially in a semicircle are symmetrical about said diameter.

5. The sensor of claim 1, wherein:
   said at least two voltage electrodes are disposed at a clearance distance from each other; and
   said at least four substantially circular current electrodes that are disposed in two semicircles comprise one of (a) four electrodes and (b) six electrodes which are disposed along semicircular configurations corresponding to and about respective said voltage electrodes.

6. The sensor of claim 5, wherein said at least two voltage electrodes are disposed on a diameter of said front wall and said at least four substantially circular current electrodes are disposed symmetrically with respect to said diameter.

7. The sensor of claim 1, wherein said synthetic material of said casing comprises an insulating synthetic material.

8. The sensor of claim 7, wherein said insulating synthetic material is selected from the group consisting of polyether ether ketone and glass.

9. The sensor of claim 1, wherein said measuring electrodes comprise liquid resistant conductors.

10. The sensor of claim 9, wherein said liquid resistant conductors comprise a material selected form the group consisting of steel, tantalum, nickel-molybdenum-iron alloy and artificial carbon.

11. The sensor of claim 1, wherein said casing is capable of fitting into a 25 mm connection socket.

12. The sensor of claim 1, wherein said sensor has an installation length of less than 10 mm.

* * * * *